(12) United States Patent
Jabri et al.

(10) Patent No.: US 7,627,084 B2
(45) Date of Patent: Dec. 1, 2009

(54) IMAGE ACQUISITION AND PROCESSING CHAIN FOR DUAL-ENERGY RADIOGRAPHY USING A PORTABLE FLAT PANEL DETECTOR

(75) Inventors: Kadri Nizar Jabri, Waukesha, WI (US); Gopal Biligeri Avinash, Menomonee Falls, WI (US); John Michael Sabol, Sussex, WI (US); Renuka Uppaluri, Pewaukee, WI (US)

(73) Assignee: General Electric Compnay, Schenectady, NY (US)

( * ) Notice: Subject to any disclaimer, the term of this patent is extended or adjusted under 35 U.S.C. 154(b) by 114 days.

(21) Appl. No.: 11/731,535

(22) Filed: Mar. 30, 2007

(65) Prior Publication Data

US 2008/0240357 A1  Oct. 2, 2008

(51) Int. Cl.
*H05G 1/10* (2006.01)
(52) U.S. Cl. .......................... 378/62; 378/154
(58) Field of Classification Search ................ 378/98.8, 378/62, 205, 207, 154, 155
See application file for complete search history.

(56) References Cited

U.S. PATENT DOCUMENTS

| | | | | |
|---|---|---|---|---|
| 6,007,243 | A | * 12/1999 | Ergun et al. | .................. 378/197 |
| 2003/0103597 | A1 | * 6/2003 | Sklebitz | ........................ 378/63 |
| 2003/0169848 | A1 | * 9/2003 | Jabri et al. | .................. 378/98.9 |
| 2004/0264626 | A1 | * 12/2004 | Besson | ........................... 378/4 |

* cited by examiner

*Primary Examiner*—Hoon Song
(74) *Attorney, Agent, or Firm*—Fletcher Yoder (57) ABSTRACT

A mobile dual-energy X-ray imaging system is presented. The mobile dual-energy X-ray imaging system is a digital X-ray system that is designed both to acquire original image data and to process the image data to produce an image for viewing. The system has an X-ray source and a portable flat-panel digital X-ray detector. The system is operable to produce a high energy image and low energy image, which may be decomposed to produce a soft tissue image and a bone image for further analysis of the desired anatomy. The system is disposed on a carrier to facilitate transport. The imaging system has an alignment system for facilitating alignment of the flat-panel digital detector with the X-ray source. The imaging system also comprises an anti-scatter grid and an anti-scatter grid registration system for removing artifacts of the anti-scatter grid from images.

20 Claims, 5 Drawing Sheets

IMAGE ACQUISITION AND PROCESSING CHAIN FOR DUAL-ENERGY RADIOGRAPHY USING A PORTABLE FLAT PANEL DETECTOR

BACKGROUND

The present disclosure relates generally to dual-energy imaging and, in particular, to techniques for producing and processing dual-energy images with a mobile dual-energy imaging system having a portable flat-panel digital detector.

Medical diagnostic and imaging systems are ubiquitous in modern health care facilities. Currently, a number of modalities exist for medical diagnostic and imaging systems. These include computed tomography (CT) systems, X-ray systems (including both conventional and digital or digitized imaging systems), magnetic resonance (MR) systems, positron emission tomography (PET) systems, ultrasound systems, nuclear medicine systems, and so forth. Such systems provide invaluable tools for identifying, diagnosing and treating physical conditions and greatly reduce the need for surgical diagnostic intervention. In many instances, these modalities complement one another and offer the physician a range of techniques for imaging particular types of tissue, organs, physiological systems, and so forth.

Digital imaging systems are becoming increasingly widespread for producing digital data that can be reconstructed into useful radiographic images. In one application of a digital imaging system, radiation from a source is directed toward a subject, typically a patient in a medical diagnostic application, and a portion of the radiation passes through the subject and impacts a detector. The surface of the detector converts the radiation to light photons, which are sensed. The detector is divided into an array of discrete picture elements or pixels, and encodes output signals based upon the quantity or intensity of the radiation impacting each pixel region. Because the radiation intensity is altered as the radiation passes through the subject, the images reconstructed based upon the output signals may provide a projection of tissues and other features similar to those available through conventional photographic film techniques. In use, the signals generated at the pixel locations of the detector are sampled and digitized. The digital values are transmitted to processing circuitry where they are filtered, scaled, and further processed to produce the image data set. The data set may then be used to reconstruct the resulting image, to display the image, such as on a computer monitor, to transfer the image to conventional photographic film, and so forth.

Dual-energy (DE) radiography involves the acquisition of two X-ray images at different energies within a relatively small time interval. The two images are then used to decompose the imaged anatomy and create soft-tissue and bone images. Existing digital radiography (DR) image acquisition and processing techniques were not designed for DE radiography. In addition, the application of DE imaging to mobile DR imaging systems adds several unique challenges. For example, in a mobile DR imaging system, the spatial location of the detector is not always known relative to the X-ray source, as in a fixed permanent DR imaging system. Additionally, the detector may not be mechanically fixed relative to the X-ray source and may move slightly whenever the patient moves. As a result, misalignment may occur between the X-ray source and the detector. Furthermore, mobile DR imaging systems frequently are used to obtain images of patients that are too sick to move. Consequently, these patients frequently cannot hold their breaths very easily, if at all. As a result, artifacts are created in the image when the lung volume changes between the first and second exposure.

Accordingly, techniques are needed to overcome the problems associated with mobile DR imaging systems. The techniques described herein are intended to solve one or more of the problems associated with mobile DR imaging systems.

BRIEF DESCRIPTION

A mobile dual-energy X-ray imaging system is presented. The mobile dual-energy X-ray imaging system is a digital X-ray system that is designed both to acquire original image data and to process the image data to produce an image for viewing. The system has an X-ray source and a portable flat-panel digital X-ray detector. The system has a wheeled-carrier to enable the system to be transported to a patient. The system is operable to produce a high energy image and low energy image of a patient, which may be decomposed to produce a soft tissue image and a bone image for further analysis of the desired anatomy. Because of the limitations of a mobile system in comparison to an installed system, a number of techniques are utilized to enhance the image acquisition, processing, and display capabilities of the mobile dual-energy X-ray imaging system.

One aspect of the present invention is that the system may utilize a respiratory sensor to perform pulmonary gating during image acquisition. Another aspect of the present invention is a system for facilitating alignment of the flat-panel digital detector with the X-ray source. Still another aspect of the present invention is a temperature correction function for compensating for temperature gradients in the flat-panel digital X-ray detector after transitioning from a low power condition to a full power condition. Yet another aspect of the present invention is anti-scatter grid registration when an anti-scatter grid is utilized. Additional aspects of the present invention are provided below.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
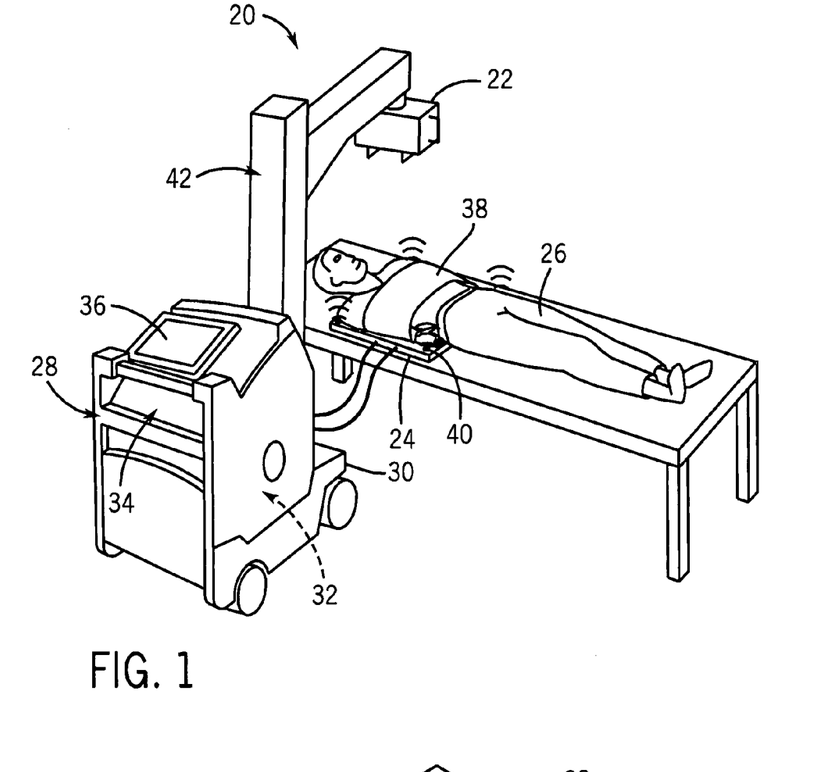
FIG. 1 is a perspective view of a dual-energy X-ray imaging system, in accordance with an exemplary embodiment of the present technique.

Although a dual-energy system is described in the foregoing description, the concepts are equally applicable to a multiple energy system as well. Referring generally to FIG. 1, a mobile dual-energy X-ray imaging system is presented, referenced generally by reference numeral 20. In the illustrated embodiment, the dual-energy X-ray imaging system 20 is a digital X-ray system that is designed both to acquire original image data and to process the image data for display in accordance with the present techniques. In particular, the system 20 is operable to produce a high energy image and low energy image, which may be decomposed to produce a soft tissue image and a bone image for further analysis of the desired anatomy.

The mobile dual-energy X-ray imaging system 20 has an X-ray source 22 and a portable flat-panel digital X-ray detector 24. The portable flat-panel digital X-ray detector 24 is operable to perform dual-energy X-ray imaging. A patient 26 is located between the X-ray source 22 and the detector 24. The detector 24 receives X-rays that pass through the patient 26 and transmits imaging data to a base unit 28. The portable flat-panel digital X-ray detector 24 is coupled by a cable to the base unit 28 and may be stored in the base unit 28 during transport. The base unit 28 houses the systems electronics 32 that process the imaging data to produce an image for viewing. In addition, the systems electronics 32 both provides and controls power to the X-ray source 22. The power for the X-ray source 22 is provided by a generator that is operable to supply the power to the X-ray source 22 to produce both a high energy image and a low energy image. The base unit 28 also has an operator workstation 34 that enables a user to control the operation of the system 20 to produce a desired image. Images produced by the systems electronics 32 are displayed on a display 36. In addition, images produced by the system 20 may be printed onto a film.

The mobile dual-energy X-ray imaging system 20 also includes several sensors to enhance operation of the system 20. In the illustrated embodiment, a respiratory sensor 38 is provided to send a signal representative of the patient's respiratory cycle to the systems electronics 32. Because movement of the portable flat-panel digital X-ray detector 24 is independent of the X-ray source 22, it is possible for the X-rays to strike the detector 24 at an angle, producing an inaccurate image of the patient 26. In the illustrated embodiment, the detector 24 has alignment transmitters 40 that are used to align the detector 24 with the X-ray source 22 to ensure that the X-rays from the X-ray source 22 strike the detector 24 at the correct angle. In the illustrated embodiment, sensors located proximate to the X-ray source 22 are adapted to receive the signals produced by the alignment transmitters 40. The system 20 is able to use the signals to triangulate the orientation and location of the detector 24 relative to the X-ray source 22 to determine if the detector 24 is aligned normal to the path of X-rays coming from the X-ray source 22. The alignment sensors may also be operable to indicate when the detector 24 is within range of the X-ray source 22. When the detector 24 and X-ray source 22 are aligned, an audible and/or a visible indicator are activated.

However, the converse arrangement may be used, i.e., the alignment transmitters 40 may be placed on the X-ray source 22 and the sensors within the detector 24. In addition, the X-ray source 22 is supported by an adjustable stand 42. Finally, the system 20 may be connected to the Internet or other communication network so that the images produced by the system 20 may be sent to a remote user, such as a radiologist's workstation.

Figure 2:
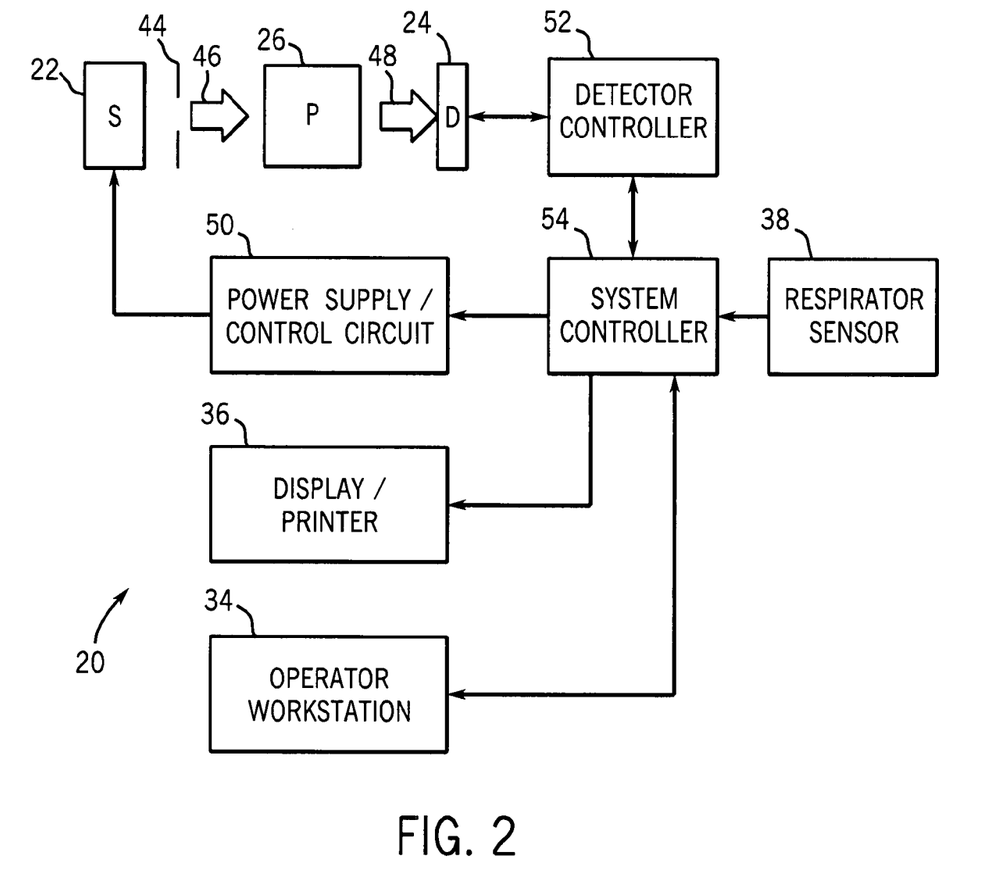
FIG. 2 is a diagrammatical overview of the dual-energy X-ray imaging system of FIG. 1, in accordance with an exemplary embodiment of the present technique.

Referring generally to FIG. 2, the mobile dual-energy imaging system 20 includes a collimator 44 positioned adjacent to the X-ray source 22. The collimator 44 permits a stream of radiation 46 to pass into a region in which a patient 26 is positioned. A portion of the radiation 48 passes through or around the patient 26 and impacts the portable flat-panel digital X-ray detector 24. As described more fully below, the X-ray detector 24 converts the X-ray photons received on its surface to lower energy photons, and subsequently to electric signals, which are acquired and processed to reconstruct an image of the features within the subject. FIG. 2 also illustrates the importance of the X-ray source 22 and the portable flat-panel digital X-ray detector 24 being in alignment. If not aligned, the portion of the radiation 48 that passes through or around the patient 26 cannot be received by the detector 24 and an accurate image of the patient 26 cannot be obtained. Furthermore, even if the detector 24 is in the direct line with the X-ray source, the detector 24 must be angled perpendicular relative to the X-ray source 22 for proper detection of the radiation 48.

The X-ray source 22 is controlled by a power supply/control circuit 50, which furnishes both power and control signals for examination sequences. Moreover, detector 24 is coupled to a detector controller 52, which commands acquisition of the signals generated in the detector 24. The detector controller 52 may also execute various signal processing and filtration functions, such as for initial adjustment of dynamic ranges, interleaving of digital image data, and so forth. Both power supply/control circuit 50 and detector controller 52 are responsive to signals from a system controller 54. In general, system controller 54 commands operation of the imaging system to execute examination protocols and to process acquired image data. In the present context, system controller 54 also includes signal processing circuitry, typically based upon a general purpose or application-specific digital computer, associated memory circuitry for storing programs and routines executed by the computer, as well as configuration parameters and image data, interface circuits, and so forth. In the illustrated embodiment, the respiratory sensor 38 provides respiratory cycle data to the system controller 54.

The system controller 54 is linked to an output device, such as the display 36 or a printer. The system controller 54 is also linked to the operator workstation 34 for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 3:
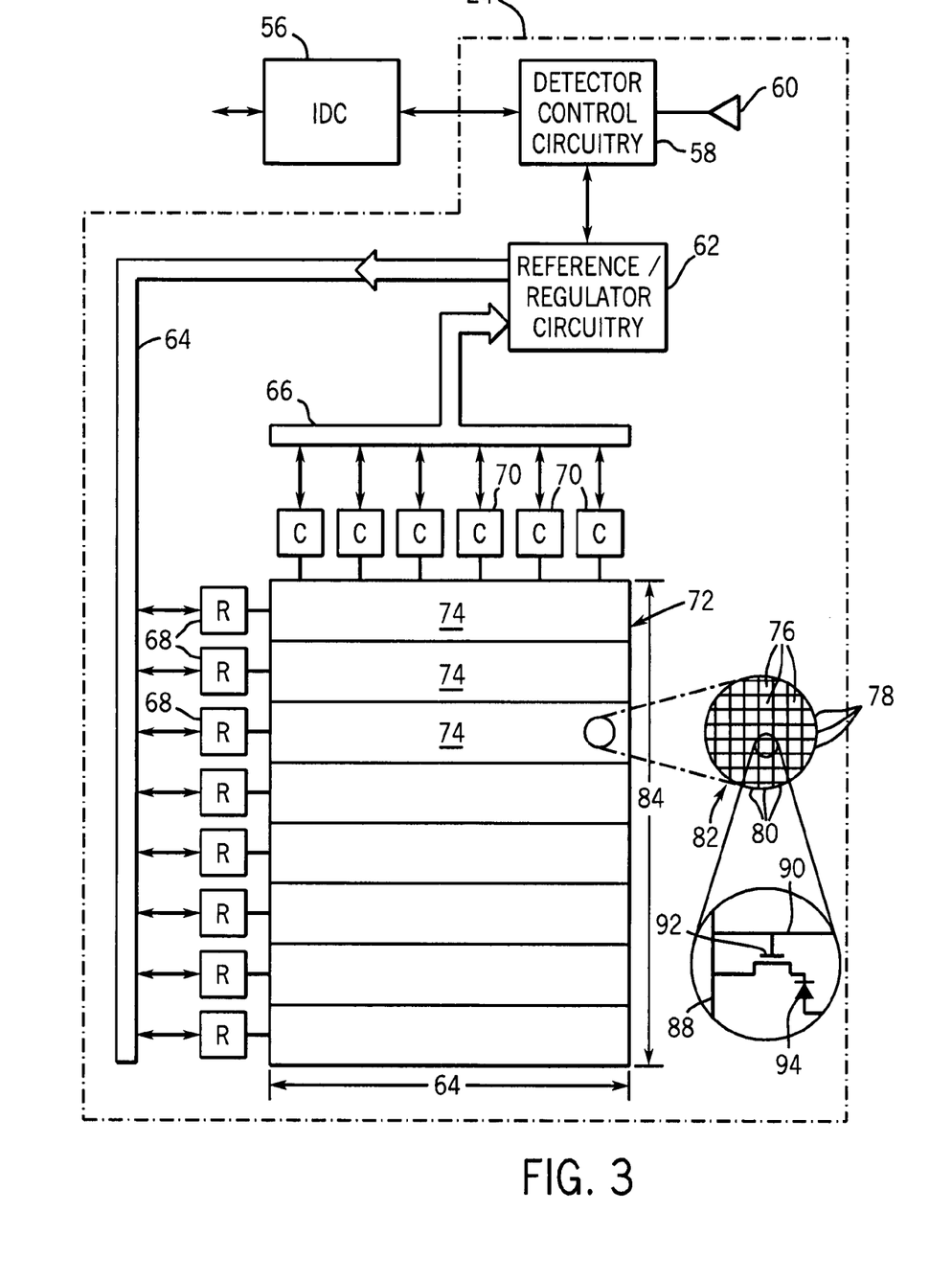
FIG. 3 is a diagrammatical representation of the functional circuitry of a detector of the system of FIG. 1, in accordance with an exemplary embodiment of the present technique.

Referring generally to FIG. 3, the functional components of the digital detector 24 are presented. In addition, an imaging detector controller or IDC 56 is presented, which will typically be configured within the detector controller 52. The IDC 56 includes a CPU or digital signal processor, as well as memory circuits for commanding acquisition of sensed signals from the detector. The IDC 56 is coupled via two-way fiber optic conductors to detector control circuitry 58 within the detector 24. The IDC 56 thereby exchanges command signals for image data within the detector during operation. The detector control circuitry 58 receives DC power from a power source 60. The detector control circuitry 58 is configured to originate timing and control commands for row and column drivers used to transmit signals during data acquisition phases of operation of the system. The detector control circuitry 58 therefore transmits power and control signals to reference/regulator circuitry 62, and receives digital image pixel data from the reference/regulator circuitry 62.

In a present embodiment, the portable flat-panel digital X-ray detector 24 consists of a scintillator that converts X-ray photons received on the detector surface during examinations to lower energy (light) photons. An array of photo detectors then converts the light photons to electrical signals, which are representative of the number of photons or the intensity of radiation impacting individual pixel regions of the detector surface. Readout electronics convert the resulting analog signals to digital values that can be processed, stored, and displayed, such as on display 36, following reconstruction of the image. In a present form, the array of photo detectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and an electrode of each column is connected to readout electronics.

In the illustrated embodiment, the portable flat-panel digital detector 24 has a row bus 64 and a column bus 66. The row bus 64 includes a plurality of conductors for enabling readout from various columns of the detector, as well as for disabling rows and applying a charge compensation voltage to selected rows, where desired. The column bus 66 includes additional conductors for commanding readout from the columns while the rows are sequentially enabled. The row bus 64 is coupled to a series of row drivers 68, each of which commands enabling of a series of rows in the detector. Similarly, readout electronics 70 are coupled to column bus 66 for commanding readout of all columns of the detector. In the present technique, image acquisition rate is increased by employing a partial readout of the detector 24. In the illustrated embodiment, the row drivers 68 and readout electronics 70 are coupled to a detector panel 72 which may be subdivided into a plurality of sections 74. Each section 74 is coupled to one of the row drivers 68, and includes a number of rows. Similarly, each of the readout electronics 70 is coupled to a series of columns. The photodiode and thin film transistor arrangement mentioned above thereby define a series of pixels or discrete picture elements 76 which are arranged in rows 78 and columns 80. The rows and columns define an image matrix 82, having a height 84 and a width 86.

Each pixel 76 is generally defined at a row and column crossing, at which a column electrode 88 crosses a row electrode 90. As mentioned above, a thin film transistor 92 is provided at each crossing location for each pixel, as is a photodiode 94. As each row is enabled by row drivers 68, signals from each photodiode 94 may be accessed via readout electronics 70, and converted to digital signals for subsequent processing and image reconstruction. Thus, an entire row of pixels in the array is controlled simultaneously when the scan line attached to the gates of all the transistors of pixels on that row is activated. Consequently, each of the pixels in that particular row is connected to a data line, through a switch, which is used by the readout electronics to restore the charge to the photodiode 94.

It should be noted that as the charge is restored to all the pixels in one row simultaneously by each of the associated dedicated readout channels, the readout electronics is converting the measurements from the previous row from an analog voltage to a digital value. Furthermore, the readout electronics are transferring the digital values from two previous rows to the acquisition subsystem, which will perform some processing prior to displaying a diagnostic image on a monitor or writing it to film. Thus, the read out electronics are performing three functions simultaneously: measuring or restoring the charge for the pixels in a particular row, converting the data for pixels in the previous row, and transferring the converted data for the pixels in a twice previous row.

Figure 4:
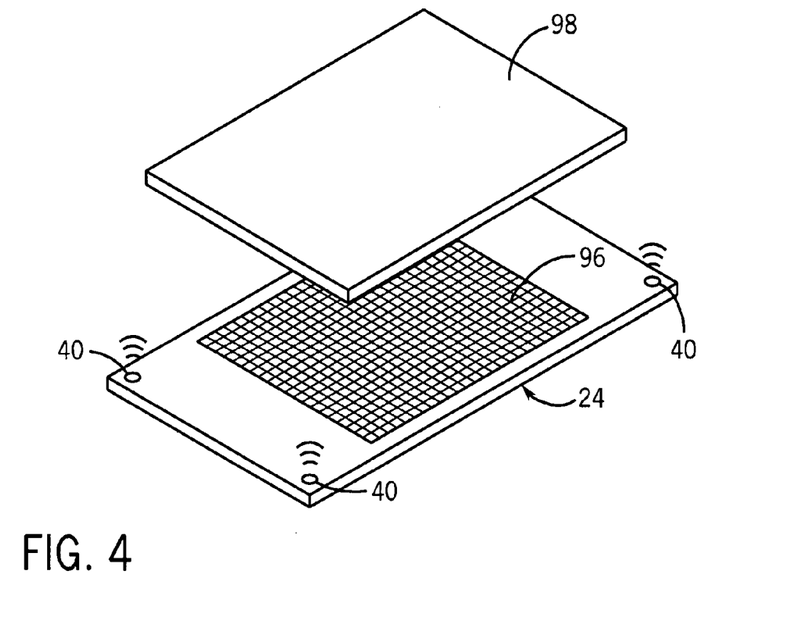
FIG. 4 is a perspective view of the detector of FIG. 1 and foam padding, in accordance with an exemplary embodiment of the present technique.

Referring generally to FIG. 4, an embodiment of the portable flat-panel digital detector 24 is presented. The detector 24 has an anti-scatter grid 96 that overlays the image matrix 82 of the portable flat-panel digital detector 24. Scattering is a general physical process whereby some forms of radiation, such as X-rays, are forced to deviate from a straight trajectory by one or more localized non-uniformities in the medium through which it passes. The anti-scatter grid 96 reduces the effect of scattering by preventing scattered X-rays from reaching the detector 24. When using such anti-scatter grids, significant misalignment between the X-ray source 22 and the grid can result in image artifacts. The alignment of the detector 24 to the X-ray source 22 is hampered by the detector 24 being independent of the X-ray source 22. In addition, because the detector 24 is placed under the region of the patient 26 to be imaged, the position of the detector 24 is determined by the position of the patient 26.

To avoid image artifacts from misalignment, transmitters 40 are used to enable alignment of the detector 24 to the X-ray source 22. Alternatively, the alignment transmitters 40 may be disposed on the anti-scatter grid 96 to ensure that the X-rays from the X-ray source 22 strike the anti-scatter grid 96 at the correct angle. The X-ray source 22 has a receiver that is operable to receive signals from the transmitters 40 and triangulate the position of the detector 24 relative to the X-ray source 22. The detector 24 and X-ray source 22 are aligned when the detector 24 is positioned so that the plane of the detector 24 is perpendicular to the X-ray beam generated by the X-ray source 22 and the detector 24 is centered relative to the X-ray source. In the illustrated embodiment, the system 20 produces a visual and/or an audile indication when the detector 24 and X-ray source 22 are aligned. Thus, enabling a user to position the detector 24 and ensure that it is in aligned prior to taking an image of the patient 26. In addition, a foam pad 98 is placed over the grid 96 in the illustrated embodiment. The foam pad 98 creates an air gap between the patient 26 and the detector 24 that also reduces the effect of scattering by preventing scattered X-rays from reaching the detector 24.

Figure 5:
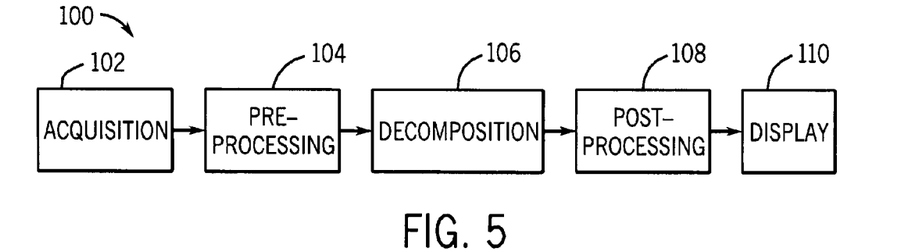
FIG. 5 is a block diagram of an image acquisition and processing technique, in accordance with an exemplary embodiment of the present technique.

Referring generally to FIG. 5, techniques for the processing of imaging data by the mobile dual-energy X-ray imaging system 20 of FIG. 1 are presented, and represented generally by reference numeral 100. Certain adaptations have been made in the following techniques because the system 20 is mobile. The first techniques in the illustrated embodiment are image acquisition techniques, represented generally by block 102. Once image acquisition is completed, pre-processing techniques are performed on the acquired image, referenced generally by block 104. After the pre-processing is completed, the acquired images are decomposed to generate a raw soft-tissue image and a raw bone image, represented generally by reference numeral 106. Next, the acquired images are post-processed, represented generally by reference numeral 108. Finally, once the post-processing is completed, the acquired images are processed for visual display, referenced generally by block 110.

Figure 6:
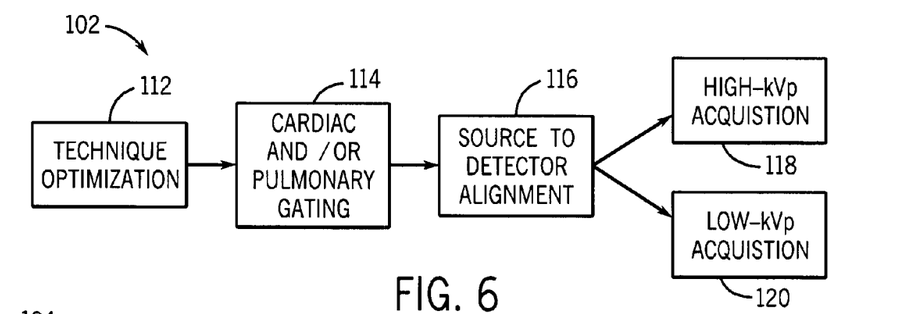
FIG. 6 is a block diagram of the image acquisition technique of FIG. 5, in accordance with an exemplary embodiment of the present technique.

Referring generally to FIG. 6, an exemplary embodiment of the image acquisition techniques 102 of FIG. 5 is presented. In the illustrated embodiment, the image acquisition techniques 102 include technique optimization techniques for use with a mobile imaging system, represented generally by block 112. Installed X-ray imaging systems typically have a much larger generator for providing power to an X-ray source. For example, fixed digital radiography systems typically have a 60-80 kW generator, whereas mobile systems have generators usually in the 15-30 kW range. Technique optimization refers to techniques that are used to account for the lower power available for generating X-rays that exists with a mobile X-ray imaging system in comparison to an installed X-ray imaging system. In the illustrated embodiment, technique optimization 112 includes adjusting the peak kilo-voltage (kVp) and copper filtration (to harden the X-ray spectrum) relative to an installed system.

Once the acquisition parameters are defined, cardiac gating and/or pulmonary gating may be performed, represented generally by reference numeral 114. Cardiac gating is a technique that triggers the acquisition of images by detector 24 at a specific point in the cardiac cycle. This reduces heart-motion artifacts in views that include the heart, as well as artifacts indirectly related to heart motion such as lung motion. Cardiac gating addresses lung/heart motion artifacts due to heart/aortic pulsatile motion. Pulmonary gating is a technique that prevents image artifacts from being created in the image when the lung volume changes between the first and second exposure. The lung volume changes can occur when the DR imaging system is used to obtain images of patients that cannot hold their breaths for very long, if at all. In one embodiment of pulmonary gating, the system 20 acquires both the high energy image and the low energy image when the lung is at its slowest motion, based on signals from the respiratory sensor 38 of FIG. 1. In an alternative embodiment of pulmonary gating, the high energy and low energy images are acquired during different respiratory cycles, but at approximately the same point in the respiratory cycle.

In the illustrated technique, an alignment of the X-ray source to the portable flat-panel digital detector 24 is performed by a user, represented generally by block 116. As discussed above, the transmitters 40 located on the detector 24 are used to align the detector 24 to the X-ray source 22. As discussed above, an audible and/or visible indication is provided when the detector 24 and X-ray source 22 are aligned. This enables an operator to know that an image taken when the indication is present will have proper alignment of the detector 24 and X-ray source 22.

During image acquisition, an X-ray image is acquired at high energy ("kVp"), represented generally by block 118. In quick succession, an X-ray image is acquired at low energy ("kVp"), represented generally by blocks 120. The low energy image typically is acquired first. The low energy exposure may last approximately 100-300 msec. The high energy exposure occurs approximately 0.5 sec later and lasts approximately 10-30 msec. The filtration of collimator 44 may be changed in between acquisitions to allow for greater separation in x-ray energies. Detector corrections may be applied to both the high energy image and low energy image, respectively. Such detector corrections are known in systems employing flat panel detectors and include techniques such as bad pixel/line correction, gain map correction, etc., as well as corrections specific to dual energy imaging such as laggy pixel corrections. In addition, the foam pad 98 described above creates an air gap between the patient 26 and the detector 24. The air gap improves image acquisition by reducing scatter.

Figure 7:
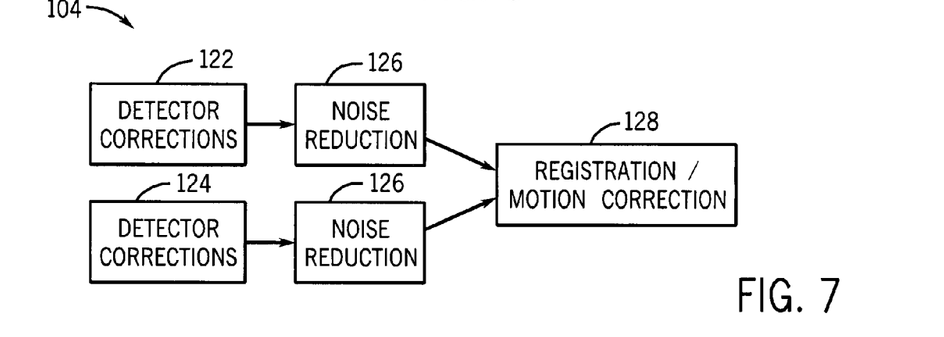
FIG. 7 is a block diagram of the image pre-processing technique of FIG. 5, in accordance with an exemplary embodiment of the present technique.

Referring generally to FIG. 7, an exemplary embodiment of the pre-processing technique 104 of FIG. 5 is presented. The pre-processing technique 104 includes a high kVp detector correction, represented generally by block 122, and a low kVp detector correction, represented generally by block 124. Existing detector correction techniques may be used such as hardware solutions including specialized anti-scatter grids, and or software solutions using convolution-based or deconvolution-based methods. Additionally, software techniques can utilize information from one image to tune parameters for the other image. In addition, detector corrections may be used to compensate for the effects of temperature on the detector 24.

With fixed X-ray imaging systems, the detector temperature remains stable once it has initially warmed up. However, mobile X-ray imaging systems are frequently turned on and off. In addition, the illustrated embodiment of the system 20 has an energy conservation feature, whereby power to the detector 24 is reduced after a period of non-use. Therefore, the temperature of the detector 24 may not be stable at a quiescent temperature when the mobile X-ray imaging system 20 is used to acquire an image. Typically, when the detector 24 is powered to full power, the detector 24 heats up due to the increase in power to the detector 24. As the detector 24 heats up, a temperature gradient exists spatially across the detector surface, which may affect the pixel offset/gain and, thereby, affect the resulting image values after an X-ray exposure. A temperature correction function is provided to compensate for the temperature gradient. The temperature correction function is based on a model of how the detector 24 heats up over time when operated at full-power. The input to the correction is the time interval between the switch to full power mode and the time of image capture. In an alternative embodiment, the detector 24 has a temperature sensor to provide an input based on the actual detector 24 temperature. The actual detector temperature is then used to establish the temperature correction function. Noise reduction also is performed. One or more noise reduction algorithms are applied to the high kVp and the low kVp images, represented generally by block 126.

Registration techniques are used to reduce motion artifacts by correcting for motion between the high kVp and the low kVp images, represented generally by block 128. The registration algorithms may be known rigid-body or warping registration routines applied to the high kVp and the low kVp images. The registration processing addresses residual structures in the soft-tissue image and/or the bone image and lung/heart motion artifacts. In addition, the registration techniques 128 include grid registration. When the anti-scatter grid 96 is used, the grid 96 can move independently of the patient 26. The grid registration corrects for any movement of the grid by aligning the grids in the high kVp image and the low kVp image.

Referring again to FIG. 5, the decomposition techniques 106 also include considerations based on the dual-energy X-ray imaging system being mobile. The two images are generally decomposed according to the dual-energy decomposition equations:

$$IS = IH/IL^{WS} \qquad (1)$$

$$IB = IH/IL^{WB} \qquad (2)$$

where IS represents the soft tissue image, IB represents the bone image, IH represents the high-energy image, IL represents the low-energy image, WS is the soft tissue decomposition parameter, WB is the bone decomposition parameter, and 0<WS<WB<1.

The special considerations for decomposition include using a spatially-variable parameter log subtraction technique that is motivated by the fact that the decomposition is region dependent under the non-optimal conditions encountered in a mobile environment. Existing log subtraction techniques assume that the parameter used for log subtraction is invariant to a location in the image. However, it has been determined through experience that the parameter is location dependent. This means that a given value of a parameter works best in one region of the image while a different value of the parameter works best in another region of the image. Here, we assume that there are "m" optimal parameters for "m" regions in an image. The spatially-variable parameter log subtraction technique is a method of segmenting the regions into "m" regions, decomposing the image using "m" different parameters and combining all the results to obtain a combined resultant image.

The main consideration for the spatially-variable parameter log-subtraction technique is to modify the log-subtraction parameter based on the amount of tissue density and put the various parts of the decomposed image back together in a seamless fashion. In the illustrated embodiment, an algorithm is used to access the high and low power image pair. The high energy image is segmented into multiple regions based on the attenuation densities to derive a mask, "M". The mask is then processed to eliminate any small holes or gaps by changing the region to their surrounding neighboring regions. The regions are then merged into a relatively small number of super-regions. For example, the super-regions may be divided into high, medium, and low tissue densities. The images are then decomposed using a standard parameter ("W") and non-standard parameters ($W_1, W_2, W_3 \ldots$). This creates a number of pairs of soft tissue images (IS, $IS_1, IS_2 \ldots$) and bone images (IB, $IB_1, IB_2 \ldots$). Intensity matching is performed for each of the soft tissue images ($IS_1, IS_2, \ldots$) to IS to obtain intensity matched images $IS_1, IS_2 \ldots$. The regions in IS are then replaced by the regions in the intensity matched images ($IS_1, IS_2 \ldots$) guided by the mask, "M". Similarly, intensity matching is performed for each of the bone images ($IB_1, IB_2 \ldots$) to IB to obtain intensity matched images $IB_1, IB_2 \ldots$. The regions in IB are then replaced by the regions in the intensity matched images ($IB_1, IB_2 \ldots$) guided by the mask, "M". As a result, the final IS and IB images have seamless, multi-parameter log extracted images.

Figure 8:
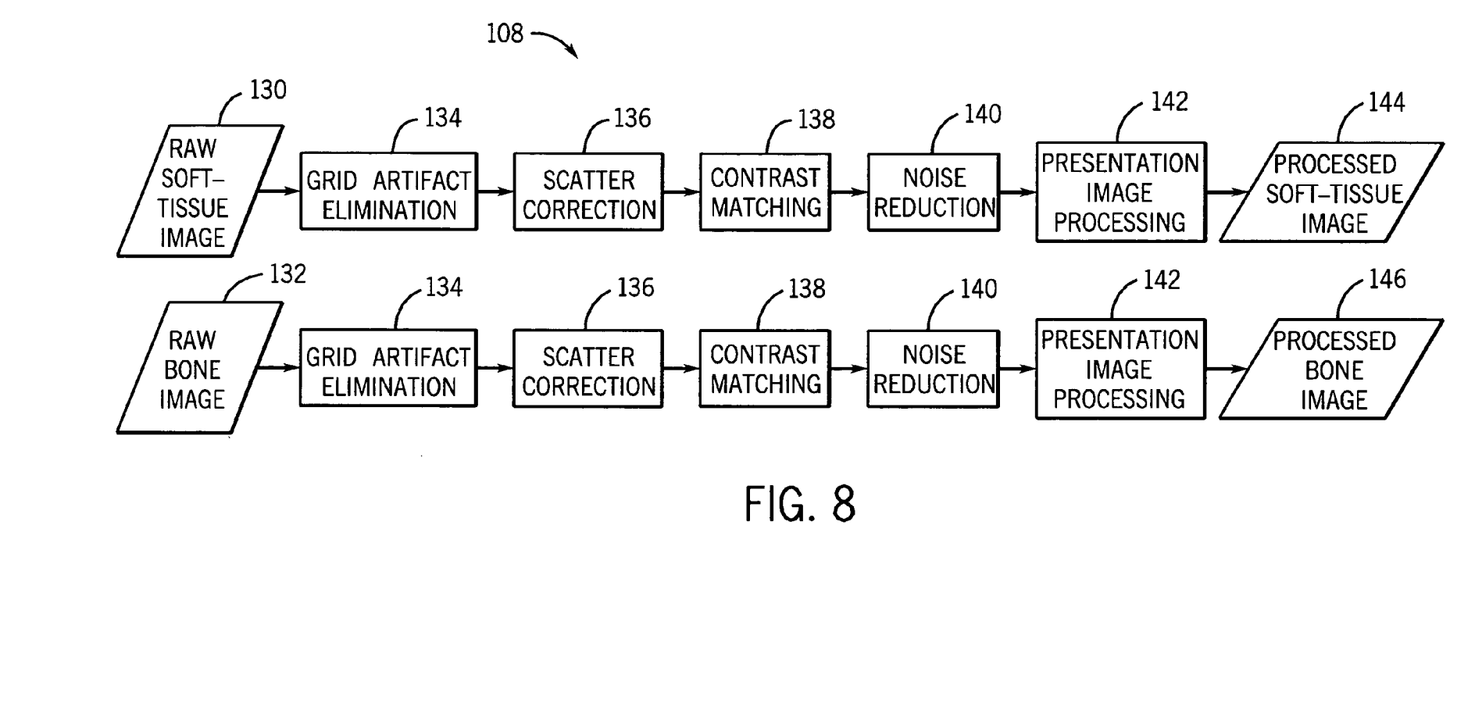
FIG. 8 is a block diagram of the image post-processing technique of FIG. 5, in accordance with an exemplary embodiment of the present technique.

Referring generally to FIG. 8, an exemplary embodiment of the image post-processing techniques 108 of FIG. 5 is presented. After decomposition, a raw soft-tissue image 130 and a raw bone image 132 are produced. During post-processing, the raw soft-tissue image 130 and the raw bone image 132 are subjected to similar processing techniques. In the illustrated embodiment, if the pre-processing techniques 104 did not remove all of the grid artifacts, grid artifact elimination techniques, represented generally by blocks 134, are used to remove any remaining grid artifacts from the raw soft-tissue image 130 and the raw bone image 132. Grid artifact elimination techniques 134 may include frequency notch filters where the resultant images are analyzed for significant spikes in the spatial frequency domain, which are then suppressed.

A scatter correction technique 136 may be used when the use of an anti-scatter grid is not possible due to clinical considerations. In the scatter correction technique 136, the high gradient edge regions are excluded from any computations. In the regions that are not in the high gradient edge regions, a weighted average of the resulting image is performed. In the regions corresponding to the edge regions, values are extrapolated based on the neighboring included regions to create a final averaged image. A fraction of the final averaged image is subtracted from the original to obtain the scatter corrected image.

Contrast matching 138 is performed match contrast of structures in raw soft-tissue image 130 and the raw bone image 132 to the corresponding structures in a standard image. For example, contrast of soft-tissue structures in raw soft-tissue image 130 (e.g., chest image) is matched to the contrast in the standard PA image. The contrast matching is performed to facilitate interpretation of the x-ray images.

One or more noise reduction techniques may be applied to the soft-tissue image 130 and the bone image 132, represented generally by block 140. The noise reduction techniques 140 address noise due to DE decomposition. Optional noise reduction algorithms may be needed depending upon the amount of scatter correction used, especially if a high-contrast image is desired. The noise reduction techniques 140 may tune the parameter settings to provide improved visualization of larger structures and to mitigate the localized, high-frequency noise.

In addition, presentation image processing, represented generally by block 142, may be performed to the raw soft-tissue image 130 and the raw bone image 132. The presentation image processing 142 includes processes such as edge enhancement, display window level and window width adjustments for optimal display. The result of the post-processing techniques 108 is a processed soft-tissue image 144 and a processed bone image 146. To allow for timely image review in a clinical environment, image processing can be accelerated by sending the raw images to a dedicated offline processor, which would then transmit the processed image back to the mobile X-ray imaging system 20 for review.

Figure 9:
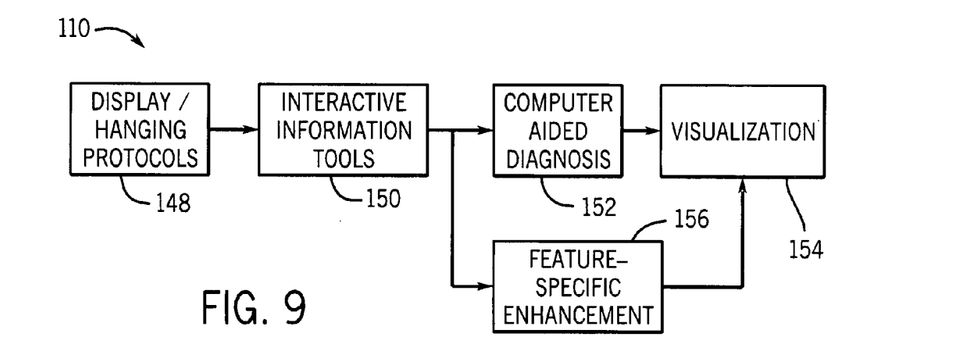
FIG. 9 is a block diagram of the image display technique of FIG. 5, in accordance with an exemplary embodiment of the present technique.

Referring to FIG. 9, an exemplary embodiment of the image display techniques 110 of FIG. 5 is presented. The display techniques 110 are intended to cover multiple display techniques including display on a monitor or by a printer. The display techniques 110 include designating display options and hanging protocols in response to user input (e.g., radiologists preferences), represented generally by block 148. These display options and hanging protocols may be customized or standardized depending on the limitations of workstation where the images are reviewed, picture archiving and communication systems (PACS), etc. For example, the resolution of the image may be adjusted depending on the display and bandwidth capabilities of the workstation where the images are viewed.

Interactive information tools, represented generally by block 150, may be utilized to make the mobile X-ray imaging system 20 more useful in emergency situations. For example, the interactive information tools 150 may provide parameters, such as distance, size, pseudo volume, and object counts. In addition, the tools 150 may enable a user to draw on the image, as well as perform stats for regions of interest.

Computer aided diagnosis (CAD) algorithms, represented generally by block 152, may be applied to one or all of the processed soft-tissue image 144, the processed bone image 146 and the standard image. The CAD algorithms 152 may be tailored to the processed soft-tissue image and processed bone image to improve performance. The processed soft-tissue image 144 and/or the processed bone image 146, along with the results of any CAD algorithms are displayed for viewing, represented generally by block 154. For example, three image types (standard, soft-tissue and bone) may be viewed dynamically on a single display, either in a time-loop or by manual stepping. This visualization technique 154 can potentially highlight pathologies that are not readily apparent in side-by-side review of images.

Feature-specific enhancement techniques, represented generally by block 156, may also be utilized. The mobile X-ray imaging system 20 may be used in situations where surgical and/or monitoring devices are common. In such situations, algorithms that highlight specific devices can help with diagnosis and patient management.

In addition, the mobile X-ray imaging system 20 may be connected wirelessly to a local or a remote workstation. Thus, the images obtained by the system 20 may be transferred quickly to a radiologist for diagnosis and treatment.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A medical imaging system, comprising:
    an X-ray source adapted to generate X-rays at a first energy level at a first point in time and a second energy level at a second point in time;
    a power supply operable to supply power to the X-ray source to generate the X-rays at the first energy level and the second energy level;
    a portable flat-panel digital X-ray detector operable to detect X-rays from the X-ray source at the first energy level and the second energy level, wherein the detector produces a first signal representative of X-ray intensity from X-rays produced at the first energy level and a second signal representative of X-ray intensity from X-rays produced at the second energy level;
    a processor-based device operable to produce material specific images from at least the first and second signals received from the detector;
    a carrier adapted to transport at least one of the X-ray source, the power supply, the digital X-ray detector and the processor-based device to a patient;
    an anti-scatter grid disposed over the detector; and
    an anti-scatter grid registration system to register the anti-scatter grid in a first material-specific image obtained from X-rays produced at the first energy level and a second material-specific image obtained from X-rays produced at the second energy level.

2. The medical imaging system as recited in claim 1, comprising:
    a sensor operable to detect a patient's respiratory cycle and to produce a signal representative of the patient's respiratory cycle.

3. The medical imaging system as recited in claim 2, wherein the medical imaging system is adapted to acquire a first image at the first energy level and a second image at the second energy level at a desired phase of a patient's respiratory cycle.

4. The medical imaging system as recited in claim 2, wherein the medical imaging system is adapted to acquire a first image at the first energy level at a given point during a first respiratory cycle and to acquire a second image at the second energy level at approximately the same given point on a subsequent respiratory cycle.

5. The medical imaging system as recited in claim 1, comprising an alignment sensor operable to produce an indication when the portable flat-panel digital X-ray detector and/or an anti-scatter grid are aligned with the X-ray source.

6. The medical imaging system as recited in claim 1, comprising a scatter-reducing pad, wherein the pad is adapted to provide a low-attenuation gap between the patient and the portable flat-panel digital X-ray detector.

7. The medical imaging system as recited in claim 1, comprising a temperature correction function to compensate detector gain for the portable flat-panel digital X-ray detector caused by a change in detector temperature.

8. The medical imaging system as recited in claim 1, wherein the processor-based device comprises an anti-scatter algorithm.

9. The medical imaging system as recited in claim 1, comprising an image decomposition process having a log subtraction algorithm comprising a spatially-variable parameter.

10. The medical imaging system as recited in claim 1, wherein the material specific images comprises a soft-tissue image and a bone image.

11. An imaging system, comprising:
    an X-ray device adapted to generate X-rays at a first energy level at a first point in time and a second energy level at a second point in time;
    a portable flat-panel digital X-ray detector operable to detect X-rays from the X-ray source at the first energy level and the second energy level, wherein the detector produces a first signal representative of X-ray intensity from X-rays produced at the first energy level and a second signal representative of X-ray intensity from X-rays produced at the second energy level;
    an image processing system coupled to the detector and operable to produce a first image based on the first signal representative of X-ray intensity and a second image based on the second signal representative of X-ray intensity;
    an anti-scatter grid disposed over the detector; and
    a grid registration system operable to register the anti-scatter grid in the first image and in the second image.

12. The imaging system as recited in claim 11, comprising a processor-based device associated with the detector, wherein the processor-based device is operable to produce a soft tissue image and a bone image from the first image and the second image.

13. The imaging system as recited in claim 11, wherein the grid registration system comprises an algorithm operable to register an image containing the anti-scatter grid in the first image with an image containing the anti-scatter grid in the second image.

14. The imaging system as recited in claim 11, comprising an alignment system operable to detect detector and/or grid position relative to the X-ray source, wherein the alignment system is coupled to the grid registration system and the gird registration system is adapted to register the anti-scatter grid in the first image and the second image based on data from the alignment system.

15. A medical imaging system, comprising:
    an X-ray source adapted to generate X-rays at a first energy level at a first point in time and a second energy level at a second point in time;
    a power supply operable to supply power to the X-ray source to generate the X-rays at the first energy level and the second energy level;
    a portable flat-panel digital X-ray detector operable to detect X-rays from the X-ray source at the first energy level and the second energy level, wherein the detector produces a first signal representative of X-ray intensity from X-rays produced at the first energy level and a second signal representative of X-ray intensity from X-rays produced at the second energy level;

an image processing system coupled to the detector and operable to produce a first image based on the first signal representative of X-ray intensity and a second image based on the second signal representative of X-ray intensity;

a carrier adapted to transport at least one of the X-ray source, the power supply, the digital X-ray detector and the processor-based device to a patient;

an anti-scatter grid disposed over the detector;

an anti-scatter grid registration system to register the anti-scatter grid in a first material-specific image obtained from X-rays produced at the first energy level and a second material-specific image obtained from X-rays produced at the second energy level; and an alignment sensor operable to produce an indication when the portable flat-panel digital X-ray detector is aligned with the X-ray source.

16. The medical imaging system of claim 15, comprising a sensor operable to detect a patient's respiratory cycle and to produce a signal representative of the patient's respiratory cycle.

17. The medical imaging system as recited in claim 16, wherein the medical imaging system is adapted to acquire a first image at the first energy level and a second image at the second energy level at a desired phase of a patient's respiratory cycle.

18. The medical imaging system as recited in claim 16, wherein the medical imaging system is adapted to acquire a first image at the first energy level at a given point during a first respiratory cycle and to acquire a second image at the second energy level at approximately the same given point on a subsequent respiratory cycle.

19. The imaging system as recited in claim 15, comprising a processor-based device associated with the detector, wherein the processor-based device is operable to produce a soft tissue image and a bone image from the first image and the second image.

20. The medical imaging system as recited in claim 19, wherein the processor-based device is linked to a data network to enable soft tissue and bone image viewing from remote locations.

* * * * *